United States Patent [19]

Buiguez et al.

[11] Patent Number: 4,934,418

[45] Date of Patent: Jun. 19, 1990

[54] PROCESS AND EQUIPMENT FOR SUPPLYING SUPERCRITICAL $CO_2$

[75] Inventors: Alexandre Buiguez, Aubagne; Michel Percy du Sert, Paris; Serge Frejaville, Mejannes-les-Ales, all of France

[73] Assignee: Carboxyque Francaise, Puteaux, France

[21] Appl. No.: 201,920

[22] Filed: Jun. 3, 1988

[30] Foreign Application Priority Data

Jun. 5, 1987 [FR] France .................................. 87 07901

[51] Int. Cl.⁵ .............................................. B65B 31/00
[52] U.S. Cl. .......................................... 141/4; 141/18; 141/59; 141/63
[58] Field of Search ...................... 141/1, 2, 4, 5, 7, 9, 141/18, 59, 63, 64, 65, 67

[56] References Cited

U.S. PATENT DOCUMENTS 3,216,209 11/1965 Krigsman .............................. 62/51
4,705,082 11/1987 Fanshawe et al. ...................... 141/4

FOREIGN PATENT DOCUMENTS 1259151 3/1961 France .
621019 4/1949 United Kingdom .

Primary Examiner—Ernest G. Cusick
Attorney, Agent, or Firm—Young & Thompson

[57] ABSTRACT

A cylinder (11) provided with a plunger tube (28) contains a mass of supercritical $CO_2$ containing 2 to 6% of dissolved helium, surmounted by a gaseous sky constituted by helium at a pressure higher than about 135 bars. Supercritical $CO_2$ can be in this way obtained which contains a few % of helium dissolved by a simple opening of the valve (27) of the cylinder. Application in the cosmetic industry.

10 Claims, 3 Drawing Sheets

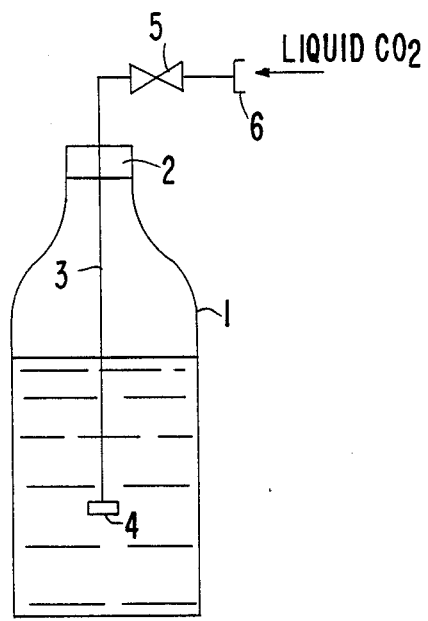
FIG.IA
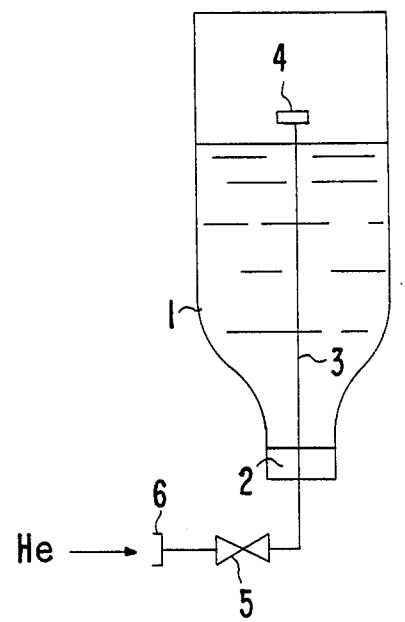
FIG.IB
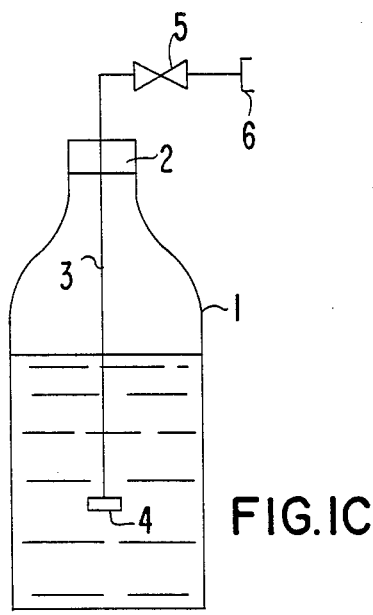
FIG.IC

PROCESS AND EQUIPMENT FOR SUPPLYING SUPERCRITICAL CO₂

FIELD OF THE INVENTION

The present invention relates to a process for supplying supercritical carbon dioxide of use, for example, in the cosmetic industry as a solvent and propellant agent.

THE PRIOR ART

The current method for supplying supercritical $CO_2$ consists in employing a store of liquid $CO_2$ at $-20°$ C., 20 bars, a high pressure pump having a plurality of stages and a refrigerating unit, which is costly and complicated.

An object of the invention is to provide a much simpler and cheaper process.

SUMMARY OF THE INVENTION

For this purpose, the invention provides a process comprising introducing a charge of liquid $CO_2$ in a pressure-resisting container and provided with fluid drawing off means, then introducing in said container a charge of helium to a pressure exceeding about 135 bars.

In order to maintain throughout the drawing off of the fluid a low content of helium in the $CO_2$, preferably, the drawing off of the $CO_2$ is stopped when the pressure drops below a limit value which is not lower than about 135 bars.

According to an advantageous manner of filling the container, there is employed as the container a cylinder provided with a plunger tube and the charge of $CO_2$ is introduced through the plunger tube, then, with the cylinder turned upside down and after a period of stabilization of the $CO_2$, the charge of helium is introduced through the plunger tube and then the cylinder is placed in the upright position for drawing off the $CO_2$.

According to another manner of carrying out the invention, a charge of liquid $CO_2$ is introduced in a first container pressure-resisting provided with fluid drawing off means, the upper part of the container is put in communication with an auxiliary container containing helium so as to supply helium to the first container at a pressure higher than about 135 bars, and this communication is maintained during the drawing off of the $CO_2$.

The invention also provides apparatus for supplying supercritical carbon dioxide. This apparatus comprises a container provided with fluid drawing off means and containing a charge which is in the form of a mass of $CO_2$ containing 3 to 6% of dissolved helium, surmounted by a gaseous sky constituted by helium at a pressure higher than about 135 bars.

In a particular embodiment, the upper part of the container communicates with an auxiliary container containing helium at a pressure higher than about 135 bars.

BRIEF DESCRIPTION OF THE DRAWINGS

Examples of carrying out the invention will now be described with reference to the accompanying drawings, in which:

FIGS. 1A–1C illustrate the steps for filling the container;

DETAILED DESCRIPTION OF THE INVENTION

Figure 1:
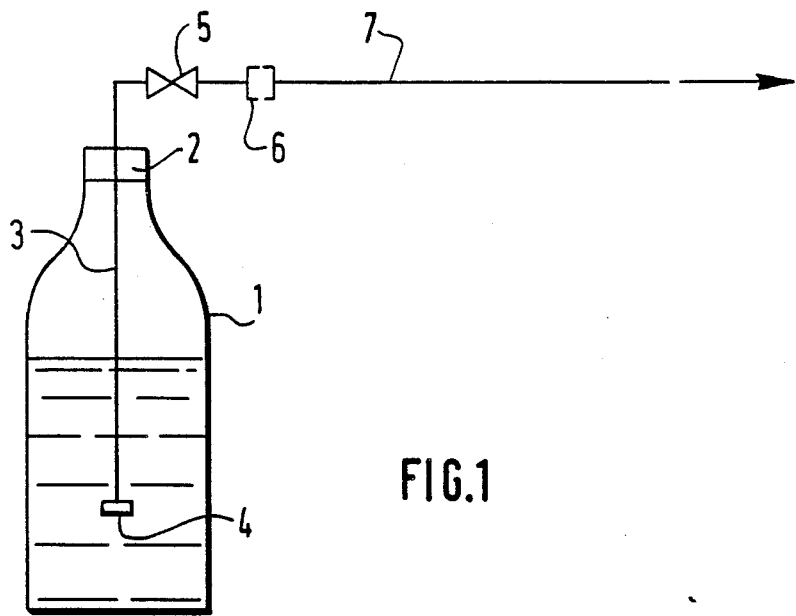
FIGS. 1 and 2 illustrate two examples of the process according to the invention.

Shown in FIG. 1 in longitudinal section is a steel cylinder 1 whose neck is provided with a plug 2 through which extends a plunger tube 3 which has at its lower end a calibrated orifice 4. The tube 3 extends down to a level which is distinctly above the bottom of the cylinder and will be defined hereinafter.

Outside the cylinder, the tube 3 is provided with a stop valve 5 and terminates in a coupling 6 for the connection of a utilization pipe 7.

The cylinder 1 is filled in the following manner.

There is introduced in the cylinder through the tube 3 a charge of liquid $CO_2$ coming from a store of $CO_2$ at $-20°$ C., 20 bars, by means of a circulation pump and a heater which brings it to about $0°$ C. for reasons related to the resilience of the steel from which the cylinder 1 is made. The $CO_2$ has a purity of 99.998% and, by weighing the cylinder, a given quantity of the $CO_2$ is measured out. This quantity, which must be sufficient to ensure that the calibrated orifice 4 is immersed, corresponds for example to a volume of liquid equal to one half of the volume of the cylinder FIG. 1A.

The cylinder is then allowed to return to ambient temperature, which constitutes a $CO_2$ stabilization phase lasting at least two hours.

The cylinder is then placed upside down (FIG. 1B) by any suitable handling means. The calibrated orifice 4 then emerges from the liquid and there is allowed a period, corresponding to a new stabilization phase on the order of 10 min, to ensure that the liquid is well assembled and the liquid-vapor equilibrium is reached again.

A charge of helium of high purity (less than 5 ppm of water, less than 5 ppm of oxygen) is then introduced through the tube 3 until a pressure of about 160 bars is reached. This pressure is chosen as high as possible, but such that, for the foreseeable maximum ambient temperature (for example $+50°$ C.), it remains below the service pressure of the cylinder 1.

The cylinder is then put back into its upright position (FIG. 1C) and, after a new period of stabilization on the order of one hour, it is ready to supply supercritical $CO_2$ merely by opening the valve 5.

The cylinder is then in the state shown in FIG. 1, that is, it contains a charge consisting of:

a mass of supercritical $CO_2$ containing a certain quantity of dissolved helium, a gaseous sky at about 160 bars consisting solely of helium.

Analyses have shown that, when the pressure of the helium drops from 160 bars to about 135 bars, the content of dissolved helium in the $CO_2$ is low and is maintained at a substantially constant value of 3 to 4%, while this content suddenly increases when the pressure drops below about 135 bars. Consequently, if it is only desired to draw off $CO_2$ with a low content of helium, the drawing off will be stopped when the pressure, which drops with the lowering of the level of the fluid, reaches a limit value no lower than this value of about 135 bars.

For this purpose, and as shown in FIG. 1, the tube 3 may be lowered only to a level corresponding to a volume of the gaseous sky which provides the pressure of about 135 bars. If the volume of the filling of the liquid $CO_2$ is previously chosen for example to be equal to roughly one half of the capacity of the cylinder, as mentioned hereinbefore, the level in question is deduced by calculation. As a variant, if it is preferred to draw off practically the whole of the fluid, the tube 3 will extend down almost to the bottom of the cylinder and the initial volume of the liquid $CO_2$ will be calculated correspondingly.

However, in these two cases, the pipe 7 will conduct a gaseous $CO_2$-helium mixture, or pure helium, at the end of the drawing off. In order to avoid this, the procedure illustrated in FIG. 2 may be used: with the cylinder initially containing liquid $CO_2$ at roughly one half the volume, the tube 3 descends almost to the bottom of the cylinder and the utilization pipe 7 is provided with a pressure-controller valve 8 which is closed when the pressure drops to the limit value of about 135 bars. The drawing off thus automatically stops and the cylinder is then changed.

Figure 3:
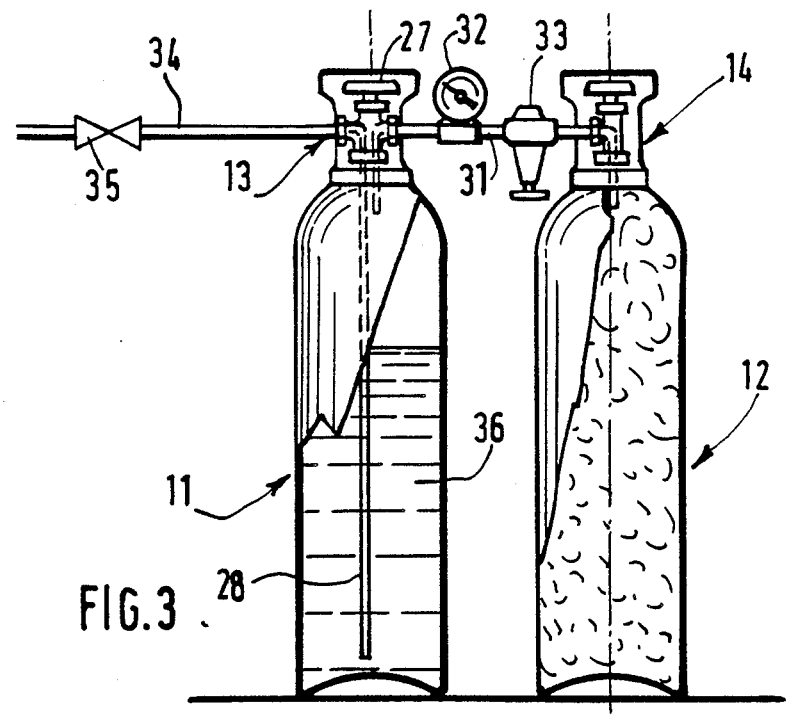
FIG. 3 is an elevational view, partly in section, of apparatus according to the invention.

FIG. 3 shows apparatus comprising two cylinders 11 and 12 having the same dimensions and equipped with a valve 13 and 14 respectively.

Figure 4:
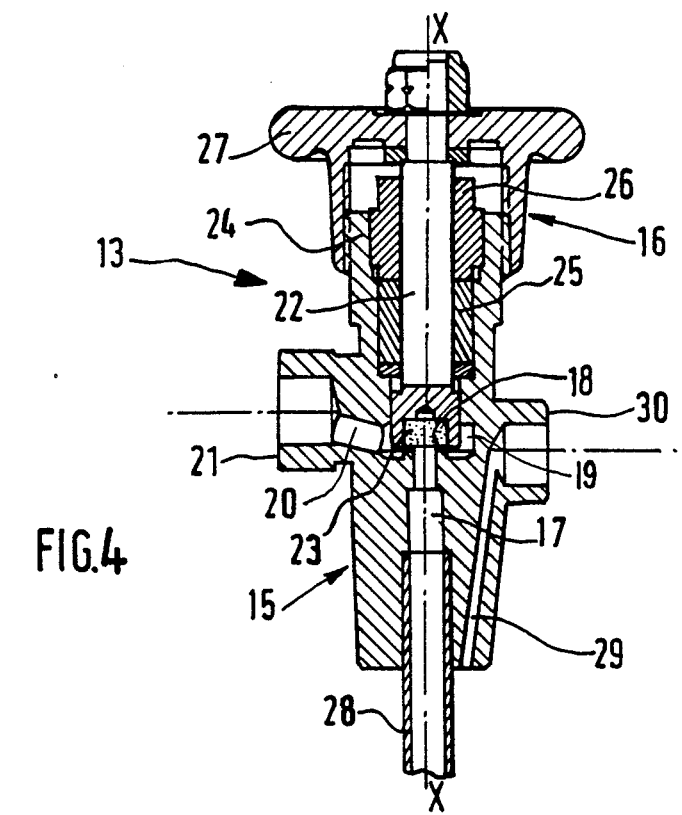
FIG. 4 is a longitudinal sectional view of a detail of the apparatus of FIG. 3.

The valve 13, which is shown to an enlarged scale in FIG. 4, comprises a body 15 having a vertical general axis X—X, and an operating device 16. The lower part of the body 15, fixed in the neck of the cylinder 11, defines an inlet duct 17 which terminates in a seat 18 and opens onto a chamber 19. A drawing off duct 20, which terminates in a main coupling 21, extends laterally from the chamber 19, and the latter has an upper orifice in which is slidable the lower end of the operating rod 22 of the valve which is provided with a valve closure member 23 capable of being applied against the seat 8.

The upper part of the body 15 forms a tube 24 which surrounds the rod 22. The operating device 16 comprises, in addition to the rod 22, a sealing element 25 which surrounds the rod and is compressed in the tube 24 by a packing nut 26, and an operating wheel 27 screwed on the upper end portion of the tube 24. The plunger tube 28, which extends down to almost the bottom of the cylinder 11, is fitted in the inlet duct 17 and the lower part of the body 15 includes an additional bore 29 which puts the upper part of the cylinder in communication with a lateral auxiliary coupling 30.

The valve 14 is identical to the valve 13 except that its body has no bore 29 and no auxiliary coupling 30. Further, the cylinder 12 has no plunger tube, so that the inlet duct 17 of the valve 14 directly opens onto the upper part of this cylinder.

As can be seen in FIG. 3, the coupling 30 of the valve 13 is connected to the coupling 21 of the valve 14 by a pipe 31 provided with a pressure gauge 32 and a pressure reducer 33. Further, a utilization pipe 34 provided with a stop valve 35 is connected to the coupling 21 of the cylinder 11.

Figure 2:
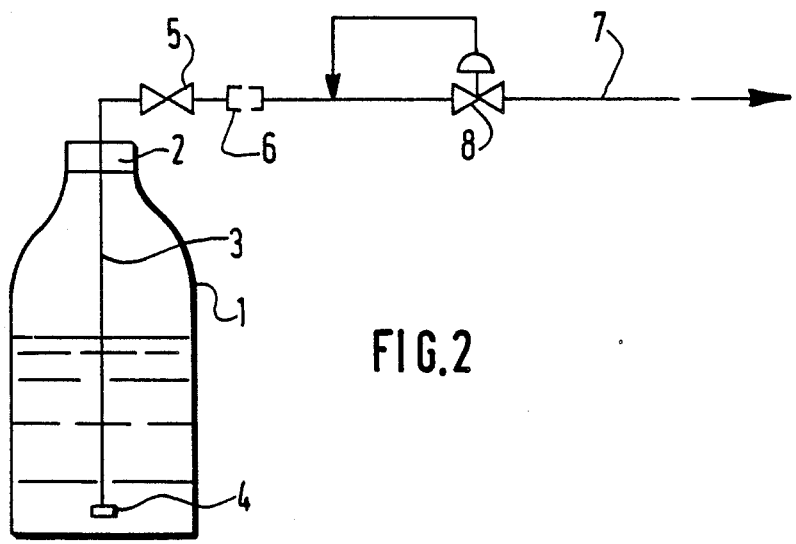

Initially, the cylinder 12 contains helium at a pressure distinctly higher than 135 bars, for example 200 bars; the valve 14 is closed and the cylinder 11 is filled up to a predetermined level with liquid $CO_2$, in the manner described with reference to FIGS. 1 and 2, through the pipe 34.

Then, with the valve 35 closed, the pressure reducer 33 is set to an outlet pressure P which is at least equal to about 135 bars and the valve 14 of the cylinder 12 is opened. The $CO_2$ is in this way pressurized at the pressure P and is in the supercritical state. The cylinder 11 then contains a mass 36 of supercritical $CO_2$ containing about 3 to 6% of dissolved helium surmounted by a gaseous sky containing solely helium.

The supercritical $CO_2$ may then be drawn off through the pipe 34 by opening the valve 35. As the level of the $CO_2$ descends, helium travels from the cylinder 12 to the cylinder 11 and the latter remains constantly at the same pressure P. This remains true so long as the pressure of the cylinder 12 remains higher than the value P; consequently, by suitably choosing the initial level of the liquid $CO_2$ in the cylinder 11, the whole of the $CO_2$ may be drawn off at this same pressure P.

As a variant, the pressure reducer 33 may be dispensed with. The $CO_2$ would then be supplied at a pressure progressively decreasing from the initial pressure prevailing in the cylinder 12.

We claim:

1. A process for supplying supercritical carbon dioxide, comprising introducing liquid $CO_2$ into a pressure-resisting container having fluid drawing off means, introducing helium into said container until the pressure in said container is higher than about 135 bars at ambient temperature, whereby the carbon dioxide is in a supercritical state with about 3–6% of helium dissolved therein, drawing off carbon dioxide through said drawing off means, and discontinuing said drawing off when the pressure in said container has fallen to a value no less than about 135 bars at ambient temperature.

2. A process according to claim 1, wherein said drawing off means comprises a plunger tube that extends downwardly into said container, the quantity of liquid $CO_2$ introduced into the container and the length of said tube being so chosen that the pressure in the container does not fall below about 135 bars at ambient temperature at the end of the drawing off of the $CO_2$.

3. A process according to claim 1, wherein said drawing off means comprises a pipe having a pressure control valve.

4. A process according to claim 1, and supplying said helium to said container from an auxiliary container containing helium at a pressure substantially higher than said pressure higher than about 135 bars at ambient temperature, and maintaining said containers in communication with each other during said drawing off of the $CO_2$.

5. A process according to claim 4, and expanding the helium to said pressure higher than about 135 bars at ambient temperature between said auxiliary container and the first-mentioned container.

6. A process for supplying supercritical carbon dioxide, comprising introducing liquid $CO_2$ into a pressure-resisting container having fluid drawing off means comprising a plunger tube that extends downwardly into said container, inverting the container so that the tube extends upwardly, introducing helium through said tube into said inverted container until the pressure in said container is higher than about 135 bars at ambient temperature, whereby the carbon dioxide is in a supercritical state with about 3–6% of helium dissolved therein, once more inverting the container so that the tube again extends downwardly, drawing off carbon dioxide through said downwardly extending tube, and discontinuing said drawing off when the pressure in said container has fallen to a value no less than about 135 bars at ambient temperature.

7. Apparatus for supplying supercritical carbon dioxide, comprising a container having means for drawing off fluid carbon dioxide therefrom, said container containing a mass of supercritical carbon dioxide containing about 3–6% of dissolved helium and surmounted by a gaseous sky constituted by helium, the pressure in said container being higher than about 135 bars at ambient temperature, and means for discontinuing said carbon dioxide drawing off when the pressure in said container has fallen to a value no less than about 135 bars at ambient temperature.

8. Apparatus according to claim 7, wherein the pressure in said container is about 160 bars at ambient temperature.

9. Apparatus according to claim 7, and an auxiliary container containing only helium at a pressure higher than about 135 bars at ambient temperature, said auxiliary container communicating with an upper part of the first-mentioned container.

10. Apparatus according to claim 9, and a pressure reducer in communication between said auxiliary container and said first-mentioned container, the pressure in said auxiliary container being substantially higher than the pressure in said first-mentioned container and said pressure reducer reducing the pressure of helium flowing from said auxiliary container to said first-mentioned container.

* * * * *